United States Patent
Feng (10) Patent No.: US 7,323,887 B2
(45) Date of Patent: Jan. 29, 2008

(54) CONDUCTIVITY SENSOR AND MANUFACTURING METHOD THEREFOR

(75) Inventor: Chang-Dong Feng, Long Beach, CA (US)

(73) Assignee: Rosemount Analytical Inc., Irvine, CA (US)

( * ) Notice: Subject to any disclaimer, the term of this patent is extended or adjusted under 35 U.S.C. 154(b) by 0 days.

(21) Appl. No.: 11/396,403

(22) Filed: Mar. 30, 2006

(65) Prior Publication Data

US 2006/0219564 A1    Oct. 5, 2006

Related U.S. Application Data (60) Provisional application No. 60/667,568, filed on Apr. 1, 2005.

(51) Int. Cl.
*G01R 27/08* (2006.01)
*G01N 27/02* (2006.01)
*G01N 11/00* (2006.01)

(52) U.S. Cl. ............... 324/724; 324/446; 324/441; 324/698; 73/54.01

(58) Field of Classification Search ............... 324/724, 324/722, 691, 441, 446, 449, 76.11, 158.1, 324/698; 702/57, 65, 108, 117; 73/53.01, 73/54.01, 335.05; 205/81, 83
See application file for complete search history.

(56) References Cited

U.S. PATENT DOCUMENTS

| | | | | |
|---|---|---|---|---|
| 5,017,875 A * | 5/1991 | Hori et al. | .................. | 324/446 |
| 5,693,577 A | 12/1997 | Krenik et al. | ................ | 437/228 |
| 6,057,175 A * | 5/2000 | Milla et al. | ................. | 438/113 |
| 6,146,510 A * | 11/2000 | Leader et al. | .......... | 204/403.01 |
| 6,196,057 B1 * | 3/2001 | Discenzo | ................... | 73/54.01 |
| 6,196,059 B1 * | 3/2001 | Kosslinger et al. | ........ | 73/61.49 |
| 6,362,438 B1 * | 3/2002 | Chong et al. | ............... | 174/262 |
| 6,781,389 B1 * | 8/2004 | Colvin et al. | ............... | 324/724 |
| 6,972,152 B2 * | 12/2005 | Taggert et al. | .............. | 428/209 |
| 6,974,916 B2 * | 12/2005 | Sakai | ......................... | 174/262 |
| 7,084,639 B2 * | 8/2006 | Wu et al. | .................... | 324/601 |
| 2002/0167322 A1 | 11/2002 | He et al. | .................... | 324/441 |
| 2006/0006884 A1 * | 1/2006 | Yamada et al. | ............. | 324/724 |
| 2006/0011474 A1 * | 1/2006 | Schulein et al. | ....... | 204/403.01 |

FOREIGN PATENT DOCUMENTS

DE    198 42 735 A1    3/2000

(Continued)

OTHER PUBLICATIONS

International Search Report and Written Opinion from Application No. PCT/US2006/011802, filed Mar. 31, 2006.

(Continued)

*Primary Examiner*—Vincent Q. Nguyen
*Assistant Examiner*—Hoai-An D. Nguyen
(74) *Attorney, Agent, or Firm*—Westman, Champlin & Kelly, P.A.

(57) ABSTRACT

A contacting-type conductivity sensor includes a plurality of electrodes disposed on a distal surface of a substrate. The substrate includes a plurality of vias through which electrical interconnection to the electrodes is accomplished. The conductivity sensor can employ two or four electrodes and may have a temperature sensitive element disposed on the distal surface. The electrodes may be patterned or otherwise deposited using semiconductor processing techniques.

15 Claims, 8 Drawing Sheets

FOREIGN PATENT DOCUMENTS

DE  102 29 210 A1  1/2004
EP  1 411 348 A1  4/2004

OTHER PUBLICATIONS

"ENDURANCE Conductivity Sensors," Product Data Sheet, Emerson Process Management, Aug. 2004, pp. 1-12.

"Theory and Application of Conductivity," Application Data Sheet, Emerson Process Management, Aug. 2004, pp. 1-5.

"ENDURANCE Sanitary Flange Conductivity Sensors," Product Data Sheet, Emerson Process Management, Jun. 2005, pp. 1-7.

Tang, Boon et al., "Toward a Miniature Wireless Integrated Multisensor Microsystem for Industrial and Biomedical Applications," IEEE Sensors Journal, vol. 2, No. 6, Dec. 2002, pp. 628-635.

* cited by examiner

FIG. 1A

(PRIOR ART)

CONDUCTIVITY SENSOR AND MANUFACTURING METHOD THEREFOR

CROSS-REFERENCE TO RELATED APPLICATION

The present application is based on and claims the benefit of U.S. provisional patent application Ser. No. 60/667,568, filed Apr. 1, 2005, the content of which is hereby incorporated by reference in its entirety.

BACKGROUND OF THE INVENTION

Conductivity measurement sensors are well known in the art and are used to measure the conductivity of a fluid, such as a liquid or a dispersion of solids suspended in a liquid. Conductivity sensors are often used to investigate the properties of electrolytes in solution, such as the degree of dissociation, the formation of chemical complexes, and the hydrolysis. The conductivity of a fluid may also be used to measure a wide variety of other parameters, such as the amount of contaminants in drinking water and a measure of chemical concentrations in industrial processes. Applications such as these involve the determination of conductivities in many physical environments.

The units of conductivity are Siemens/cm, which are identical to the older unit of mhos/cm. Conductivity measurements cover a wide range of solution conductivity from pure water at less than $1\times10^{-7}$ S/cm to values in excess of 1 S/cm for concentrated solutions.

Figure 1A:
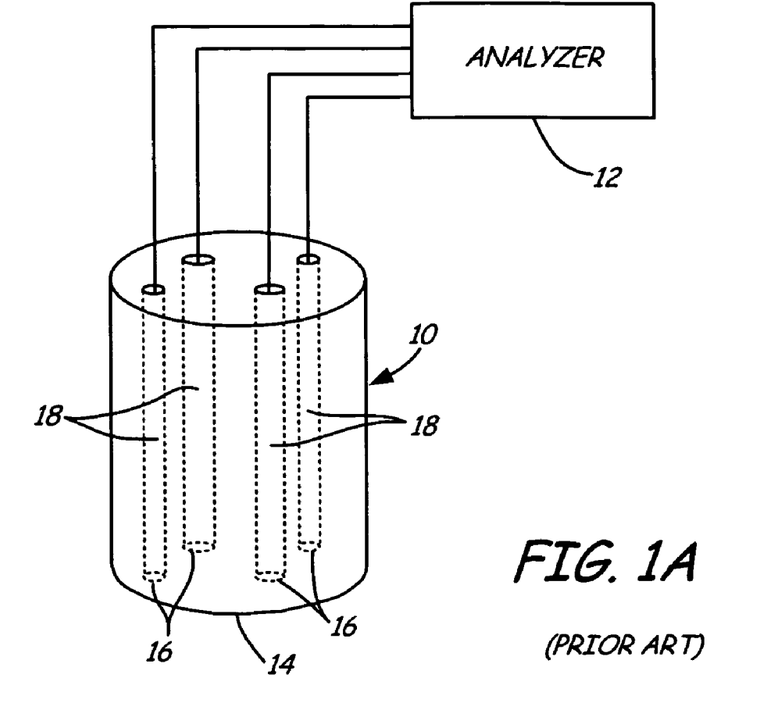
FIG. 1A is a diagrammatic view of a four-electrode contacting conductivity sensing system in accordance with the prior art.
Figure 1B:
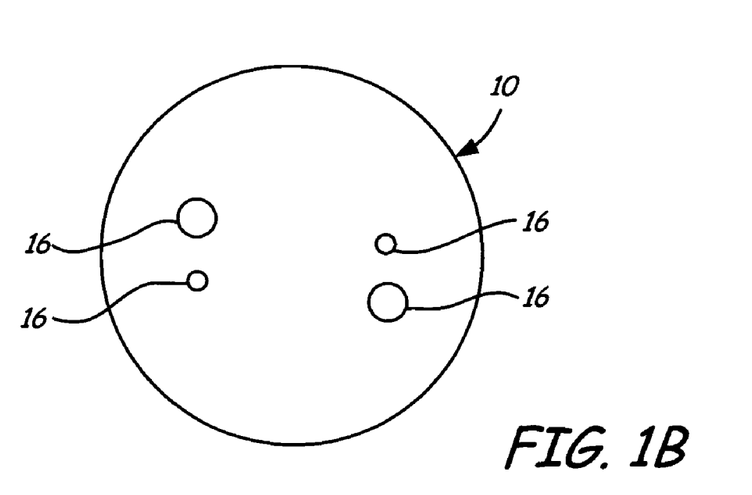
FIG. 1B is a bottom plan view of a four-electrode contacting-type conductivity sensor.

One conductivity measurement technique includes contacting a solution with electrically conducting electrodes. For example, one contacting conductivity measurement technique employs a sensor with two metal or graphite electrodes in contact with the electrolyte solution. An alternating current (AC) voltage is applied to the electrodes by the conductivity analyzer, and the resulting AC current that flows between the electrodes is used to determine the conductance. Contacting-type conductivity sensors generally employ two, or sometimes four, contacting electrodes, which physically contact the sample solution. In the case of four-electrode contacting sensors, the four-electrodes are exposed to the sample solution and a current is passed through one pair of electrodes. A voltage change between the other pair of electrodes is then measured. Based on the current and voltage, the conductivity of the liquid is calculated. Traditionally, contacting-type conductivity sensors, such as two or four-electrode sensors, are made by inserting conductive rods, (made of stainless steel, titanium, graphite, etc.) in a plastic tube, which rods are then sealed with epoxy along their length. The cross section of one end of the plastic tube is then used to expose the electrodes to the sample solution. FIG. 1A is a diagrammatic view of a four-electrode contacting-type conductivity sensor 10 in accordance with the prior art. Sensor 10 is coupled to a suitable conductivity analyzer 12. Distal end 14 of sensor 10 exposes distal ends 16 of conductive rods 18 to a sample solution disposed proximate distal end 14. FIG. 1B is a bottom plan view of sensor 10 illustrating distal ends 16 of rods 18.

Recently, contacting-type conductivity sensors, such as two and four-electrode conductivity sensors have been made by using semiconductor-like, planar manufacturing technologies. The electrodes are deposited on a passivated silicon wafer through suitable processing techniques, such as thin/thick film technology. Conductivity sensors manufactured in accordance with such semiconductor processing techniques can be mass-produced resulting in reduced size and cost of such sensors. However, the reduction in size of semiconductor-based conductivity sensors creates other manufacturing difficulties. Providing a semiconductor-based contacting-type conductivity sensor design that facilitated low-cost semiconductor-based manufacturing techniques would further benefit the art.

SUMMARY OF THE INVENTION

A contacting-type conductivity sensor includes a plurality of electrodes disposed on a distal surface of a substrate. The substrate includes a plurality of vias through which electrical interconnection to the electrodes is accomplished. The conductivity sensor can employ two or four electrodes and may have a temperature sensitive element disposed on the distal surface. The electrodes may be patterned or otherwise deposited using semiconductor processing techniques.

DETAILED DESCRIPTION OF ILLUSTRATIVE EMBODIMENTS

Figure 2A:
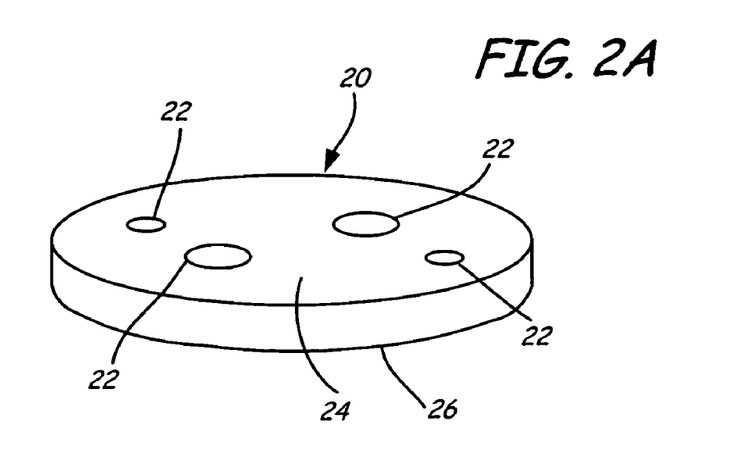
FIG. 2A is a perspective view of a substrate with which embodiments of the present invention are particularly advantageous.

FIG. 2A is a perspective view of a substrate with which embodiments of the present invention are particularly useful. Substrate 20 is illustrated in the form of a disc, but can take any suitable form. Generally, however, in order to facilitate semiconductor processing techniques and manufacturing methods, substrate 20 is relatively flat and thin. Substrate 20 can be formed out of any material that is amenable to semiconductor processing techniques and manufacturing methods. As such, substrate 20 can be formed of any suitable ceramic, glass, or combination thereof. Substrate 20 is substantially non-conductive in comparison to metal conductors, and inorganic. Suitable examples of materials for substrate 20 include silicon, zirconium oxide, aluminum oxide, Pyrex, or any other suitable material. In accordance with an embodiment of the present invention, substrate 20 includes a number of through holes or vias 22. Each of vias 22 extend from fluid contacting, distal surface 24 to interior, proximal surface 26.

Figure 2B:
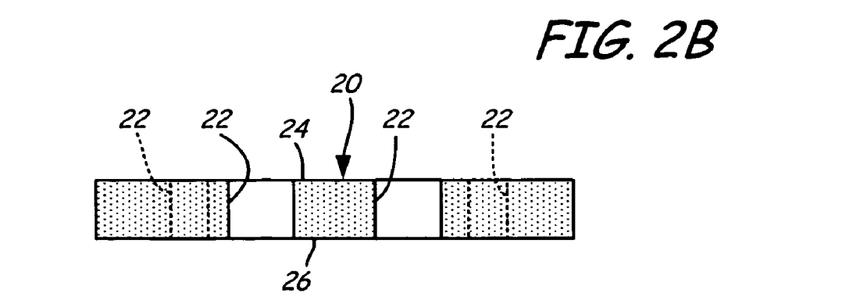
FIG. 2B is a cross sectional view of the substrate illustrated in FIG. 2A.

FIG. 2B is a cross sectional view of substrate 20. FIG. 2B illustrates holes or vias 22 extending from distal, sample contacting surface 24 to proximal surface 26. Vias 22 can be formed in accordance with any suitable techniques including semiconductor-processing techniques including etching processes, such as wet etching and/or dry etching such as reactive ion etching (RIE). Moreover, the vias can be generated using other suitable techniques including mechanical/laser drilling.

Figure 2C:
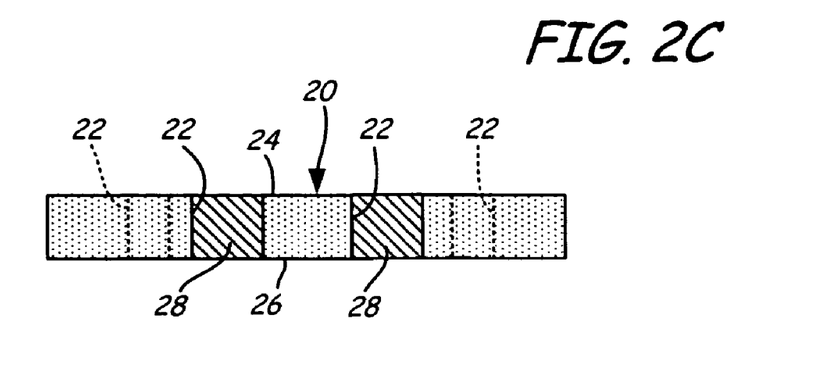
FIG. 2C is a cross sectional view of a substrate having a plurality of vias filled with a metal in accordance with an embodiment of the present invention.

FIG. 2C is a cross sectional view of substrate 20 where vias 22 are filled with a conductive metal. Each of vias 22 is at least partially filled with conductive metal 28 extending through the entire length of the via from surface 24 to surface 26. Conductive metal 28 is bonded directly to the inner diameter surfaces of vias 22 using suitable techniques forming a hermetic seal. In one example, the metal can be deposited using electron-beam vacuum deposition. However, other semiconductor processes that transfer materials onto a semiconductor material can be used such as physical vapor deposition (PVD), electrochemical deposition (ECD), molecular beam epitaxy (MBE) and atomic layer deposition (ALD). While FIG. 2C illustrates vias 22 filled completely by metal 28, it is contemplated that a portion of the via proximate the inner diameter of the via could be filled with metal and then the remaining portion, (inner diameter of the metal) could be later filled with any suitable inorganic sealing material. The deposition of metal 28 within vias 22 thus generates a "metalized" via extending between distal surface 24 and proximal surface 26 thereby generating an electrical path between the two surfaces along the via. The metalized via may have metal 28 completely filling the via, or metal 28 may only partially fill the via as long as metal 28 extends from surface 24 to surface 26. If metal 28 partially fills a via 22, then a suitable sealing agent, such as a glass frit, can be used to generate the final hermetic seal within vias 22.

Figure 2D:
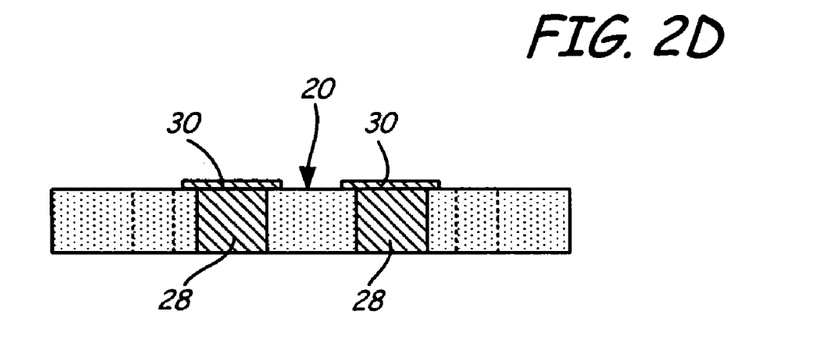
FIG. 2D is a cross sectional view of the sensor illustrated in FIG. 2C having electrodes deposited on the metal-filled vias in accordance with an embodiment of the present invention.

FIG. 2D is a diagrammatic view of substrate 20 with electrodes 30 deposited proximate and in contact with metal 28. Electrodes 30 can be formed of any suitable conductor that is chemically resistant. Examples of such suitable materials include, without limitation, platinum and gold. As with the deposition of metal 28, the deposition of electrodes 30 can be effected using any suitable thin or thick film techniques. Examples include suitable deposition processes such as physical vapor deposition, chemical vapor deposition, electrochemical deposition, molecular beam epitaxy and automatic layer deposition. Moreover, electrode material may simply be provided in sheet form and then selectively removed to generate the electrodes. Suitable semiconductor removal processes include etching processes, such as wet etching or dry etching.

Figure 2E:
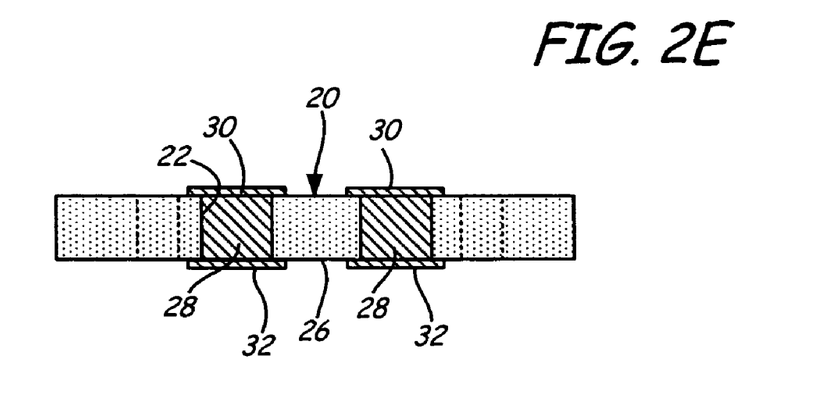
FIG. 2E is a cross sectional view of a conductivity sensor in accordance with an embodiment of the present invention during an intermediate stage of manufacture.

FIG. 2E illustrates substrate 20 having electrodes 30 disposed proximate and contacting metal 28 in vias 22. Additionally, FIG. 2E illustrates a metal transition layer 32 electrically coupled to proximal ends of metal 28 at or proximate proximal surface 26. Transition layers 32 facilitate the subsequent attachment of electrical connectors, such as pins or wires. The material selected for transition layers 32 can be the same as that of metal 28, and/or the pins or conductors that will subsequently be attached. Moreover, transition layers 32 can also be any suitable alloy, or combination of metals, that is able to effectively bond to metal 28 and the interconnect.

Figure 2F:
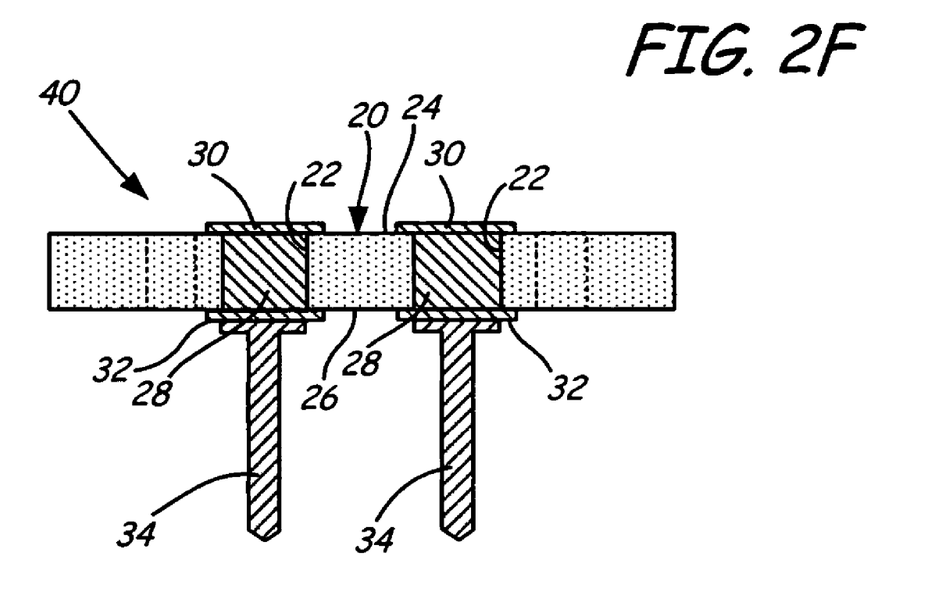
FIG. 2F is a diagrammatic view of a contacting-type conductivity sensor in accordance with an embodiment of the present invention.

FIG. 2F is a cross sectional view of a semiconductor-based contacting-type conductivity sensor in accordance with an embodiment of the present invention. Sensor 40 includes substrate 20 having a plurality of vias 22 filled by an electrically conductive metal 28. Sensor 40 includes electrodes 30 disposed proximate distal surface 24 of substrate 20, which electrodes 30 are adapted to pass an electrical current through a solution to measure the conductivity of the solution. Pins 34 are electrically connected to transition layers 32. Pins 34 are thus electrically coupled directly to electrodes 30. The design of sensor 40 provides an inorganic conductivity sensor where the distal surface is hermetically sealed from proximal surface 26. It is preferred that every electrode in contact with the sample solution have an electrical interconnect as disclosed with respect to sensor 40. Further, additional electrical features, such as a temperature sensor disposed to measure the temperature of the sample solution are also preferably electrically interconnected by virtue of vias through substrate 20 filled with metal.

FIG. 3 is a perspective view of substrate 50 having vias 52 extending from distal surface 54 to proximal surface 56. FIG. 3B is a cross sectional view of substrate 50. FIGS. 3A and 3B illustrate substrate 50 as substantially identical to substrate 20 described with respect to FIGS. 2A and 2B, and, in fact, they could be the same. However, in order to better describe this additional embodiment, the substrate is provided with reference numeral 50. FIG. 3C illustrates substrate 50 having a plurality of transition rings 58 disposed about vias 52 at distal surface 54. Transition rings 58 are preferably circularly shaped having an inner diameter that is substantially equal to the inner diameter of vias 52. The shape of the outer periphery of each of transition rings 58 can vary.

Figure 3A:
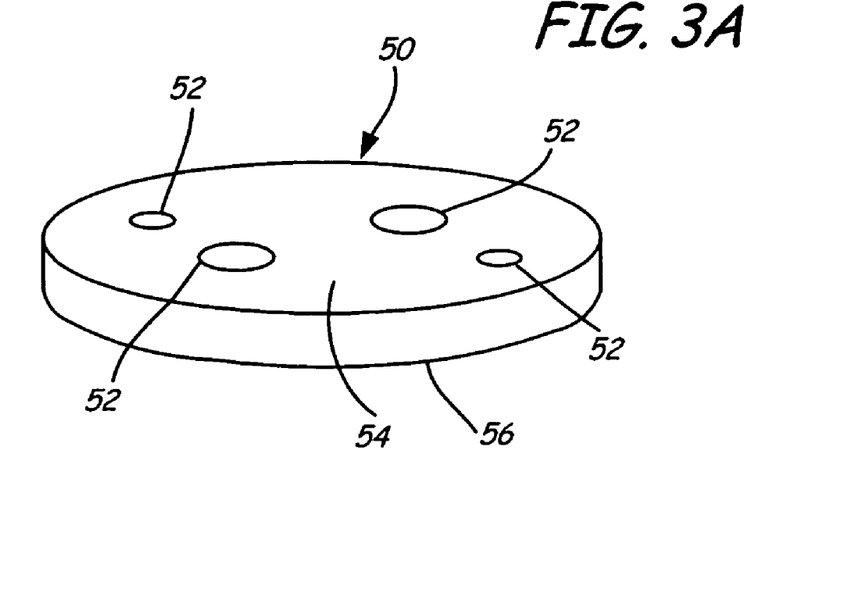
FIG. 3A is a perspective view of a substrate with which embodiments of the present invention are advantageous.
Figure 3B:
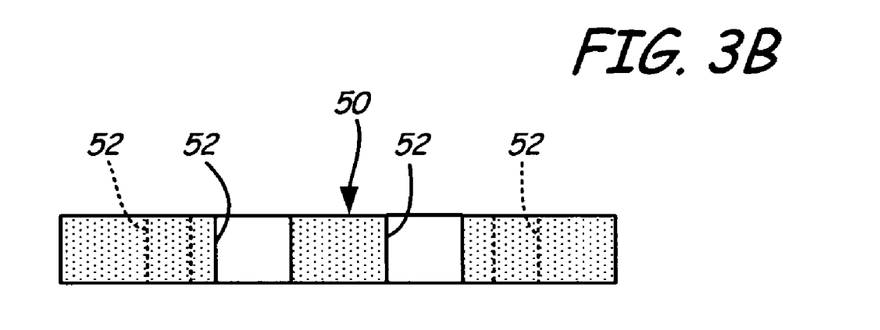
FIG. 3B is a cross sectional view of the substrate of FIG. 3A illustrating vias.
Figure 3C:
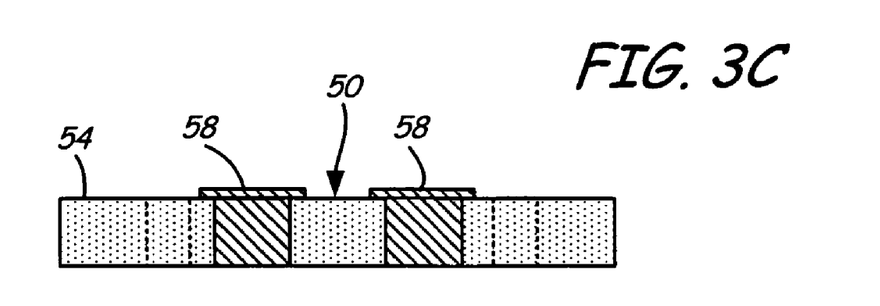
FIG. 3C is a cross sectional view of a conductivity sensor during an intermediate stage of manufacture.
Figure 3D:
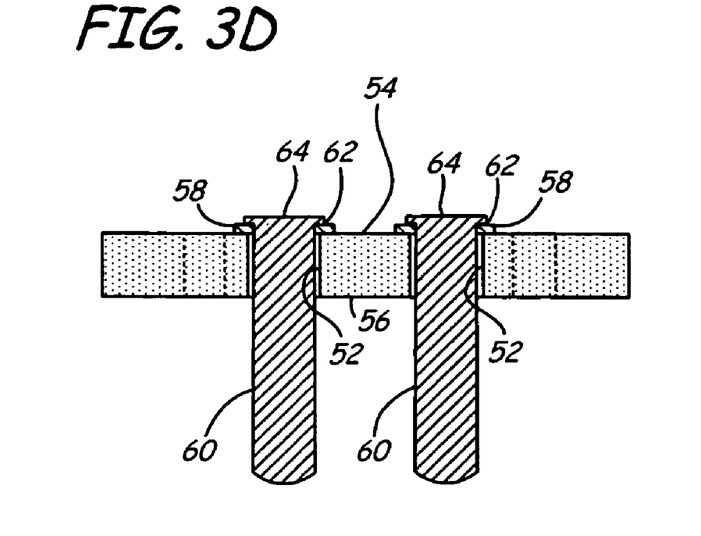
FIG. 3D is a cross sectional view of a conductivity sensor during an intermediate stage of manufacture.

FIG. 3D illustrates a plurality of pins 60 extending through vias 52 with a surface 62 of pinhead 64 in contact with transition rings 58. A suitable electrical connection, such as brazing or welding, between pins 64 and transition rings 58 generates not only an electrical connection, but an hermetic seal between distal surface 54 and proximal surface 56. Once pins 60 are suitably attached to substrate 50, electrodes 66 are deposited over, and electrically connected to pins 60. Electrodes 66 can be formed in any suitable shape.

Figure 3E:
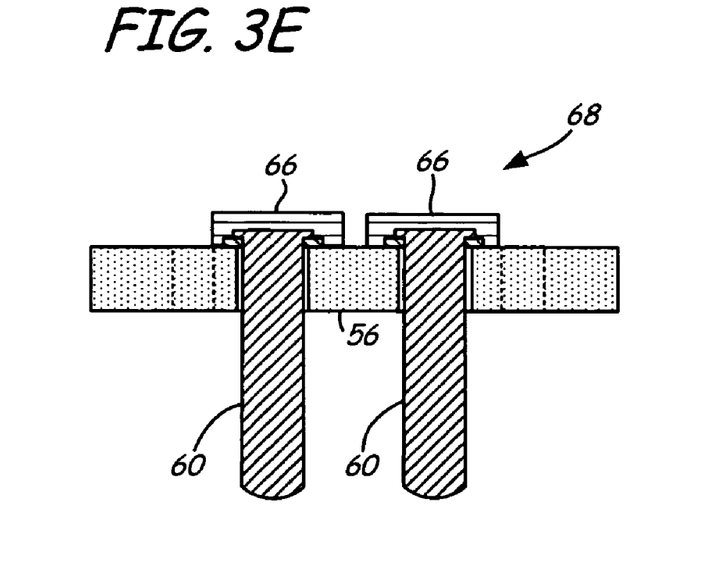
FIG. 3E is a cross sectional view of a contacting-type conductivity sensor in accordance with an embodiment of the present invention.
Figure 4A:
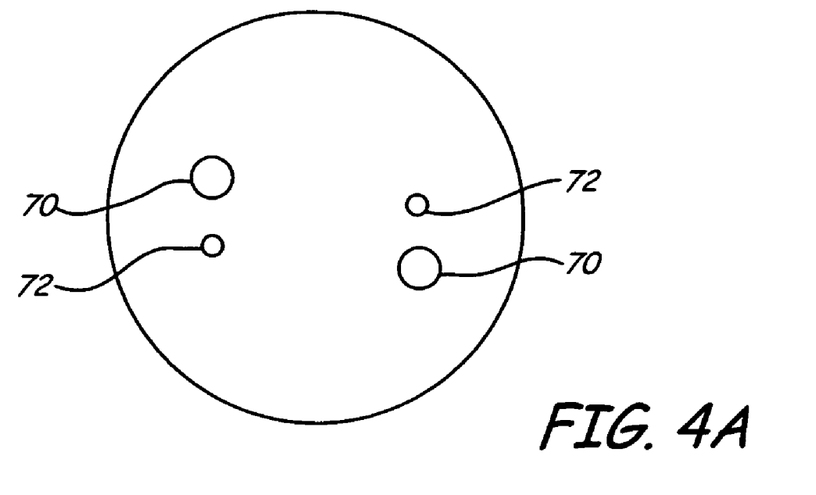
FIG. 4A is a bottom plan view of a conductivity sensor in accordance with an embodiment of the present invention.
Figure 4B:
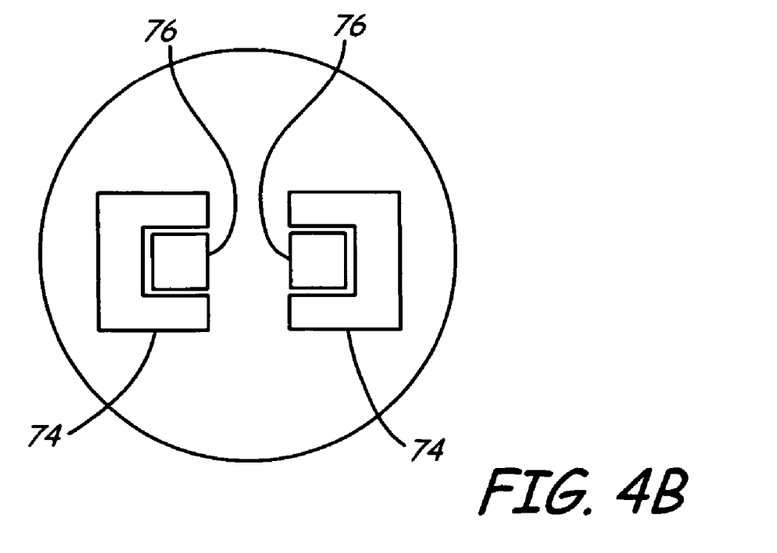
FIG. 4B is a bottom plan view of a four-electrode contacting conductivity sensor in accordance with an embodiment of the present invention.

FIG. 3E illustrates semiconductor-based contacting-type conductivity sensor 68 having a plurality of pins 60 extending through substrate 52 and generating an electrical connection between electrodes 66 and electronic circuitry (not shown) coupled to pins 60. The actual shape and configuration of the electrodes on the distal surface of the contacting-type semiconductor-based sensor can vary significantly. FIG. 4A illustrates one such arrangement with a first pair of electrodes 70 disposed adjacent to a second pair of electrodes 72. FIG. 4B illustrates yet another exemplary electrode configuration. A first pair of electrodes 74 is disposed substantially about a second pair of electrodes 76. The utilization of a plurality of pairs of electrodes in a four-electrode conductivity sensor provides some advantages over two-electrode conductivity sensors. However, it should be noted that embodiments of the present invention are equally applicable to both two-electrode sensors and four-electrode sensors. Moreover, the utilization of semiconductor processing techniques for the deposition and/or configuration of the electrodes in contact with the sample solution allows for significantly advanced electrode patterning and shaping. For example, FIG. 4B provides significantly more geometric complexity than FIG. 4A which, from a bottom plan view, appears similar to four-electrode sensors of the prior art.

Figure 4C:
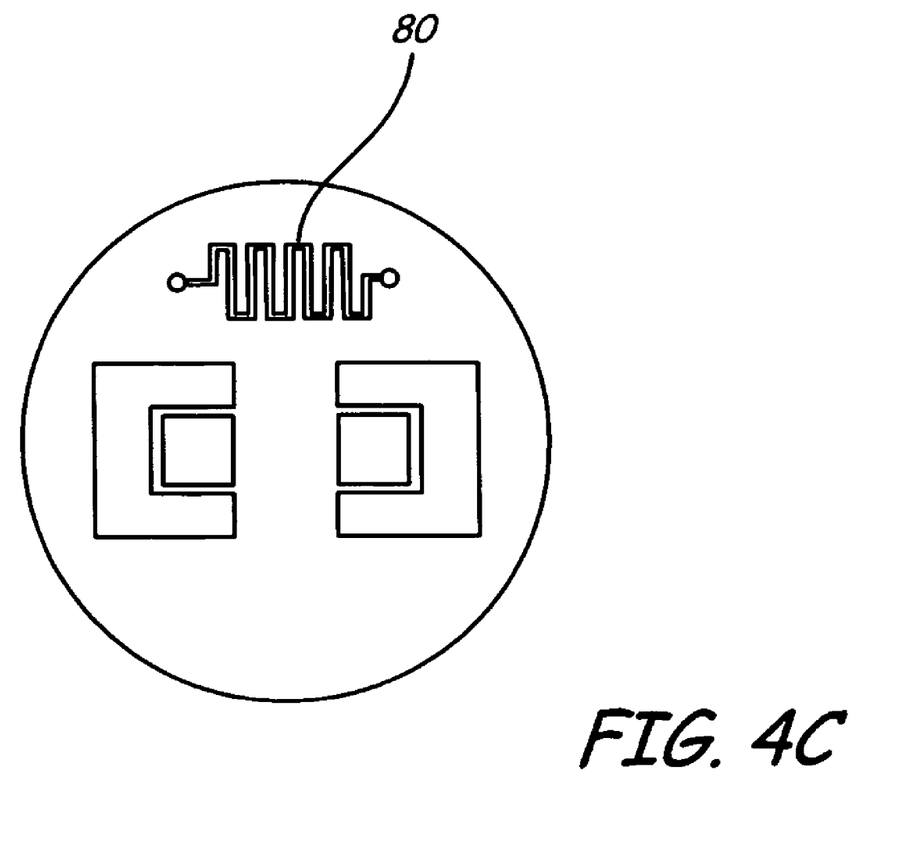
FIG. 4C is a bottom plan view of a contacting-type conductivity sensor in accordance with an embodiment of the present invention.

It is known that the conductivity of many solutions actually changes with the temperature of the solution. Thus, some conductivity sensors include a temperature sensor to provide an indication of the temperature of the sample solution. In accordance with yet another embodiment of the present invention, a temperature sensitive element 80 is disposed on the distal surface or the proximal surface of the conductivity. Element 80 can be constructed from any material that has an electrical property, such as resistance, that changes in relation to temperature, and which is amenable to semiconductor-processing techniques, such as deposition. One particular suitable metal is platinum. Further, electrical interconnects to the temperature-sensitive element on the distal surface of the sensor is are also preferably effected using metal-filled vias as disclosed above.

The substrate can additionally be mounted within a capsule or rod to complete the sensor assembly or it can be embedded or affixed to any other suitable housing. Further still, the use of semiconductor processing techniques allow for various other devices to potentially be located on the same substrate as that used for the conductivity sensor. Thus, additional sensors and/or electronics can be included, as appropriate.

Although the present invention has been described with reference to preferred embodiments, workers skilled in the art will recognize that changes may be made in form and detail without departing from the spirit and scope of the invention.

What is claimed is:

1. A fluid conductivity sensor comprising:
   an inorganic substrate having a distal, fluid contacting surface, and a proximal surface, the substrate defining a plurality of vias extending from the distal surface to the proximal surface, wherein each via contains a metal therein extending from the distal surface to the proximal surface;
   a plurality of electrodes disposed on the distal surface;
   a plurality of electrical interconnects extending beyond the proximal surface, wherein each interconnect is electrically coupled to an electrode through a respective via; and
   a temperature sensor, comprising a temperature sensitive element disposed on one of the distal surface and the proximal surface, and wherein the temperature sensitive element is electrically coupled to the plurality of electrical interconnects through the vias in the substrate.

2. The conductivity sensor of claim 1, wherein the substrate is constructed from a material selected from the group consisting of silicon, aluminum oxide, zirconium oxide, and glass.

3. The conductivity sensor of claim 1, wherein each electrode is gold.

4. The conductivity sensor of claim 1, wherein each interconnect is in the form of a pin.

5. The conductivity sensor of claim 4, and further comprising a transition material coupled to each metalized via adjacent the proximal surface, and wherein each pin is coupled to the transition material.

6. The conductivity sensor of claim 1, wherein the conductivity sensor includes four electrodes and at least four metalized vias.

7. The conductivity sensor of claim 1, wherein the plurality of electrodes are patterned on the distal surface.

8. The conductivity sensor of claim 7, wherein each of the plurality of electrodes extends beyond an outer diameter of a respective via.

9. The conductivity sensor of claim 1, wherein the metal is bonded directly to the substrate.

10. The conductivity sensor of claim 9, wherein the bond is an inorganic bond.

11. A fluid conductivity sensor comprising:
    an inorganic substrate having a distal, fluid contacting surface, and a proximal surface, the substrate defining a plurality of vias extending from the distal surface to the proximal surface;
    a plurality of vias extending from the distal surface to the proximal surface, each via having a via diameter;
    a plurality of electrodes disposed on the distal surface each electrode having at least one dimension that exceeds the diameter of its respective via; and
    a plurality of electrical interconnects each interconnect being coupled to a respective electrode and extending through the respective via; and
    a plurality of transition rings disposed about each via adjacent the distal surface, and wherein each interconnect is coupled to a respective transition ring.

12. The conductivity sensor of claim 11, wherein each interconnect is a pin.

13. The conductivity sensor of claim 12, wherein each pin is coupled to a respective transition ring by brazing.

14. The conductivity sensor of claim 12, wherein each pin is coupled to a respective transition ring by welding.

15. A fluid conductivity sensor comprising:
    an inorganic substrate having a distal, fluid contacting surface, and a proximal surface, the substrate defining a plurality of vias extending from the distal surface to the proximal surface, wherein each via contains a metal therein extending from the distal surface to the proximal surface;
    a plurality of vias extending from the distal surface to the proximal surface, each via having a via diameter;
    a plurality of electrodes disposed on the distal surface each electrode having at least one dimension that exceeds the diameter of its respective via; and
    a plurality of electrical interconnects extending beyond the proximal surface, wherein each interconnect is electrically coupled to an electrode through a respective via.

* * * * *